(12) United States Patent
Kim et al.

(10) Patent No.: US 11,313,844 B2
(45) Date of Patent: Apr. 26, 2022

(54) MULTI-CHANNEL RESISTANCE-BASED GAS SENSOR SYSTEM

(71) Applicant: ULSAN NATIONAL INSTITUTE OF SCIENCE AND TECHNOLOGY, Ulsan (KR)

(72) Inventors: Jae Joon Kim, Ulsan (KR); Subin Choi, Ulsan (KR); Kyeong-Hwan Park, Ulsan (KR)

(73) Assignee: ULSAN NATIONAL INSTITUTE OF SCIENCE AND TECHNOLOGY, Ulsan (KR)

( * ) Notice: Subject to any disclaimer, the term of this patent is extended or adjusted under 35 U.S.C. 154(b) by 398 days.

(21) Appl. No.: 16/478,623

(22) PCT Filed: Jun. 22, 2017

(86) PCT No.: PCT/KR2017/006611
§ 371 (c)(1),
(2) Date: Jul. 17, 2019

(87) PCT Pub. No.: WO2018/135711
PCT Pub. Date: Jul. 26, 2018

(65) Prior Publication Data
US 2021/0132017 A1 May 6, 2021

(30) Foreign Application Priority Data
Jan. 17, 2017 (KR) ........................ 10-2017-0008084

(51) Int. Cl.
*G01N 27/04* (2006.01)
*G01N 33/00* (2006.01)

(52) U.S. Cl.
CPC ......... *G01N 33/0022* (2013.01); *G01N 27/04* (2013.01); *G01N 33/0031* (2013.01)

(58) Field of Classification Search
CPC ...... G01N 33/0022; G01N 1/22; G01N 27/04; G01N 2027/222; G01N 33/0031
See application file for complete search history.

(56) References Cited

U.S. PATENT DOCUMENTS

| 4,542,640 A * | 9/1985 | Clifford | G01N 33/0031 422/98 |
| 5,526,280 A * | 6/1996 | Consadori | G01N 27/16 340/632 |

(Continued)

FOREIGN PATENT DOCUMENTS

| KR | 10-2005-0051725 A | 6/2005 |
| KR | 10-2007-0061042 A | 6/2007 |

(Continued)

OTHER PUBLICATIONS

Machine translation of KR101521091B (Year: 2015).*

(Continued)

*Primary Examiner* — Son T Le
*Assistant Examiner* — James I Burris
(74) *Attorney, Agent, or Firm* — Maier & Maier, PLLC

(57) ABSTRACT

In a multi-channel resistance-based gas sensor system, the multi-channel array includes gas sensor channels respectively connected to resistive type gas sensors. The pre-processing unit selects a current mode, a resistance mode, or an external resistance mode, analyzes a sensing value obtained from any one of the gas sensor channels based on the selected mode and outputs a voltage value corresponding thereto. The analog-to-digital converter (ADC) converts the voltage value to digital data. The control unit controls the pre-processing unit to execute one of the current mode for analyzing a sensing value smaller than or equal to a preset first resistance value, the external resistance mode for analyzing a sensing value greater than or equal to a preset second resistance value greater than the preset first resis- (Continued)

tance value and the resistance mode for analyzing a sensing value between the preset resistance first value and the preset second resistance value.

13 Claims, 2 Drawing Sheets

(56) References Cited

U.S. PATENT DOCUMENTS

2006/0108220 A1\*  5/2006  Betsill .................. G01N 27/128
                                                              204/412
2014/0333289 A1   11/2014  Wee et al.

FOREIGN PATENT DOCUMENTS

| KR | 20070061042 A | \* | 6/2007 | ........... G01N 27/128 |
| KR | 10-2010-0025832 A | | 3/2010 | |
| KR | 10-1521091 B1 | | 5/2015 | |
| KR | 101521091 B | \* | 5/2015 | ............. G01R 15/08 |

OTHER PUBLICATIONS

Machine translation of KR20070061042A (Year: 2007).\*
International Search Report dated Sep. 26, 2017 in corresponding International application No. PCT/KR2017/006611; 5 pages.
Office Action dated May 1, 2018 in corresponding International application No. 10-2017-0008084; 12 pages.

\* cited by examiner

MULTI-CHANNEL RESISTANCE-BASED GAS SENSOR SYSTEM

FIELD

The present invention relates to a gas sensor system; and, more particularly, to a multi-channel resistance-based gas sensor system capable of selecting and analyzing one of multiple analysis modes depending on a resistance range of sensing values (resistance values) of a target substance detected by a plurality of gas sensors.

BACKGROUND

In general, gas sensors are applied to various industrial fields such as an IOT field, an automotive air quality management field, an industrial disaster prevention field, and the like, and the gas sensors form a multi-channel sensor array to sense (detect) various types of gases. The gas sensors forming the sensor array are individually coated with different reactants that exhibit different reactions depending on gases.

Therefore, a conventional sensor monitoring device using such a multi-channel sensor array achieves high-resolution signal detection by detecting various gases (sensing values) at once by using the sensors coated with different reactants. The detected high resolution signal is analyzed by, e.g., applying a pattern recognition algorithm to the high resolution signal, and thus it is possible to detect types of gases, sensitivity (quantitative measurement), or the like.

The conventional sensor monitoring device analyzes the sensing values in the high resolution mode. Since, however, resistance values sensed by the gas sensors may have several tens to hundreds of K ohms to a few to several tens of M ohms depending on monitoring target substances, resolution by the analysis decreases at a relatively low sensing value (e.g., resistance value of 1 M ohms or smaller) or at a relatively high sensing value (e.g., resistance value of 10 M ohms or greater).

In the case of determining the resistance range of the gas sensor using a current digital-to-analog converter (DAC), the conventional sensor monitoring device flows a current suitable for the resistance value of the gas sensor while gradually controlling the current sources from the most significant bit current source (MSB current source) to the least significant bit current source (LSB current source). Since the largest current source is controlled first, an instantaneous high voltage is applied if the resistance value of the gas sensor is relatively large. Therefore, a circuit may be damaged.

SUMMARY

In view of the above, the present invention provides a multi-channel resistance-based gas sensor system capable of analyzing a sensing value (resistance value) by selecting an analysis mode suitable for a resistance range of a sensor among a current mode, a resistance mode, and an external resistance mode.

Further, the present invention provides the multi-channel resistance-based gas sensor system capable of determining a current source required for analyzing a sensing value detected by a gas sensor while sequentially switching on current sources from the least significant bit current source (LSB current source) that is the least current cell to the next upper significant bit current source.

The drawbacks to be solved by the present invention are not limited to the aforementioned drawbacks, and other drawbacks that are not mentioned will be clearly understood by those skilled in the art.

In accordance with an aspect of the present invention, there is provided a multi-channel resistance-based gas sensor system including: a multi-channel array including a plurality of gas sensor channels respectively connected to a plurality of resistive type gas sensors; a first pre-processing unit configured to select one of a current mode, a resistance mode, and an external resistance mode, analyze, based on the selected mode, a sensing value obtained from any one of the gas sensor channels among multiple sensing values detected by the resistive type gas sensors, and output a first voltage value corresponding to the analysis result; a first analog-to-digital converter (ADC) configured to convert the first voltage value to digital data; and a control unit configured to control the first pre-processing unit to execute one of the current mode, the resistance mode, and the external resistance mode. The current mode is used for analyzing, among the multiple sensing values, a sensing value that is smaller than or equal to a preset first resistance value. The external resistance mode is used for analyzing, among the multiple sensing values, a sensing value that is greater than or equal to a preset second resistance value that is greater than the preset first resistance value. The resistance mode is used for analyzing, among the multiple sensing values, a sensing value that is greater than the preset first resistance value and smaller than the preset second resistance value.

Further, the first pre-processing unit may include a first mode unit having a current digital-to-analog converter (DAC) and a first switch that connects a channel line for the gas sensors and the current DAC; a second mode unit having a resistance DAC and a second switch that connects the channel line for the gas sensors and the resistance DAC; and a third mode unit having an external resistance connected to the channel line for the gas sensors.

Further, the first mode unit may select the current mode when the first switch is switched on and the second switch is switched off.

Further, the second mode unit may select the resistance mode when the first switch is switched off and the second switch is switched on.

Further, the third mode unit may select the external resistance mode when both of the first switch and the second switch are switched off.

Further, the first pre-processing unit may further include a first current source determination unit configured to determine a current source required for analyzing each of the sensing values detected by the resistive type gas sensors while sequentially switching on a plurality of current sources having different current capacities from the least significant bit current source (LSB current source) having the least current capacity to the next upper significant bit current source.

Further, the first current source determination unit may include a first voltage comparator configured to compare the first voltage value with a preset reference voltage value, and a first successive approximation registers (SAR) digital logic unit configured to output preset n-bit number of digital data sequentially from the least significant bit to the most significant bit based on whether an output of the first voltage comparator is high or low.

Further, the multi-channel array may further include: at least one heater resistance channel connected to a temperature sensor. The multi-channel resistance-based gas sensor system described above may further include a second pre-processing unit configured to select one of the current mode, the resistance mode, and the external resistance mode, analyze a sensing value obtained from the heater resistance channel based on the selected mode, and output a second voltage value corresponding to the analysis result, and a second analog-to-digital converter (ADC) configured to convert the second voltage value to digital data.

Further, the second pre-processing unit may include a first mode unit having a current digital-to-analog converter (DAC) and a first switch that connects a channel line for heater resistance and the current DAC; a second mode unit having a resistance DAC and a second switch that connects the channel line for the heater resistance and the resistance DAC; and a third mode unit having an external resistance connected to the channel line for the heater resistance.

Further, the first mode unit may select the current mode when the first switch switched is on and the second switch is switched off.

Further, the second mode unit may select the resistance mode when the first switch is switched off and the second switch is switched on.

Further, the third mode unit may select the external resistance mode when both of the first switch and the second switch are switched off.

Further, the second pre-processing unit may further include a second current source determination unit configured to determine a current source required for analyzing the sensing value detected by the temperature sensor while sequentially switching on a plurality of current sources having different current capacities from the least significant bit current source (LSB current source) having the least current capacity to the next upper significant bit current source.

Further, the second current source determination unit may include a second voltage comparator configured to compare the second voltage value with a preset reference voltage value, and a second SAR digital logic unit configured to output preset n-bit number of digital data sequentially from the least significant bit to the most significant bit based on whether an output of the second voltage comparator is high or low.

Effect of the Invention

In accordance with the present invention, an analysis mode suitable for a resistance range of a sensor can be selected among the current mode, the resistance mode, and the external resistance mode to analyze a sensing value (resistance value). Therefore, various resistance ranges of sensing values can be analyzed at a high resolution without a decrease in the resolution by the analysis.

Further, in accordance with the present invention, a current source required for analyzing a sensing value detected by a gas sensor is determined while sequentially switching on current sources from the least significant bit current source (LSB current source) that is the least current cell to the next upper significant bit current source, thereby effectively preventing the circuit from being damaged by a high voltage caused by a relatively large resistance value of the gas sensor.

DETAILED DESCRIPTION OF THE EMBODIMENTS

Advantages and features of the present invention and methods for achieving them will become apparent from the embodiments which will be described later in detail with reference to the accompanying drawings. However, the present invention is not limited to the embodiments described herein below but may be implemented in many different forms. The embodiments are provided to make complete the disclosure of the present invention and to completely inform the scope of the present invention to those skilled in the art to which the present invention pertains. The present invention is defined only by the claims.

In describing the embodiments of the present invention, the detailed descriptions of well-known functions or configurations will be omitted if it is determined that the detailed descriptions of well-known functions or configurations may unnecessarily make obscure the spirit of the present invention. The terms to be described later are defined in view of the functions exercised in the embodiments of the present invention and may vary depending on the intention of a user or an operator and the practice. Thus, the definition of terms shall be made based on the overall contents of the subject specification.

Hereinafter, embodiments of the present invention will be described in detail with reference to the accompanying drawings.

Figure 1:
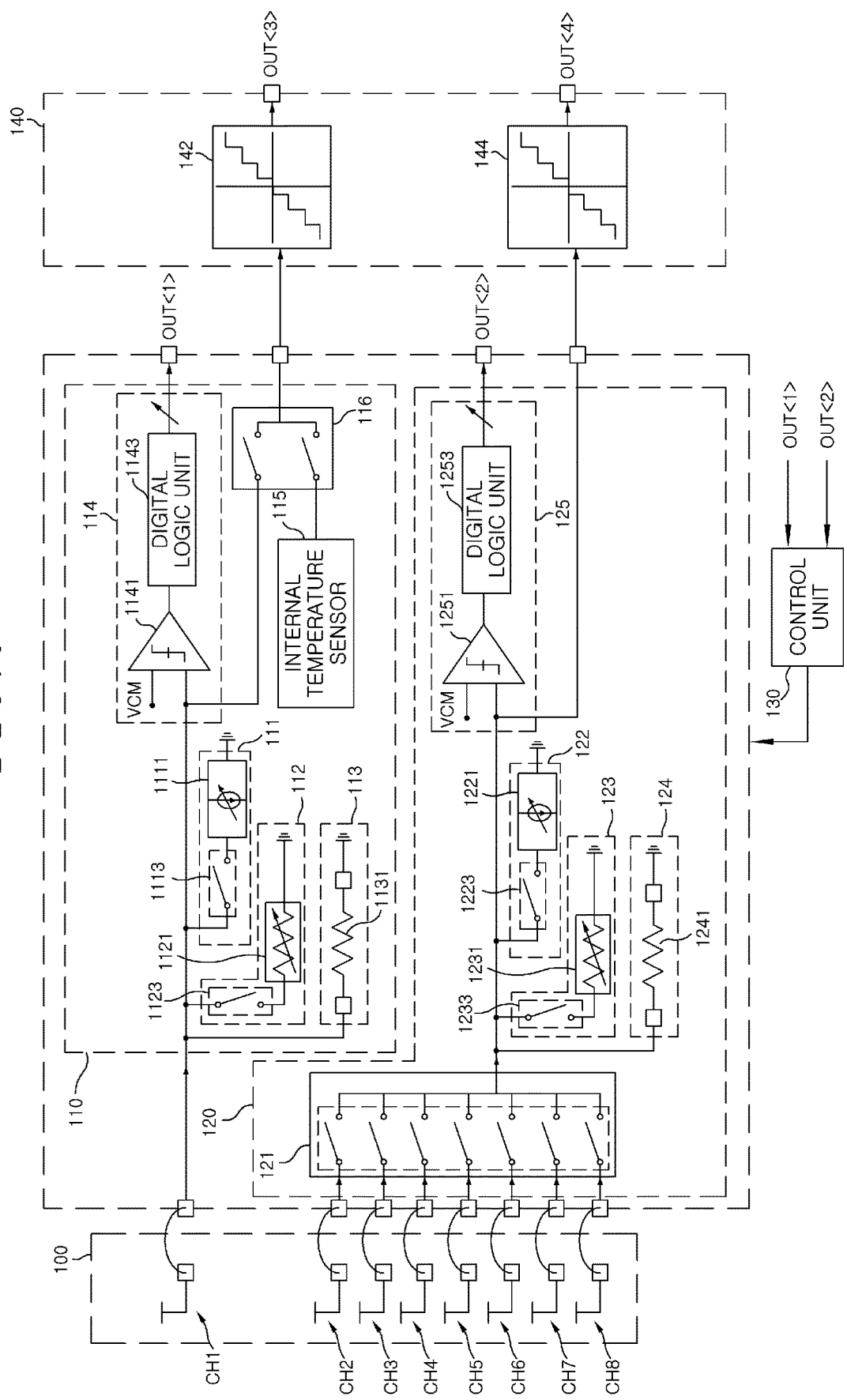
FIG. 1 is a block diagram of a multi-channel resistance-based gas sensor system according to an embodiment of the present invention.

FIG. 1 is a block diagram of a multi-channel resistance-based gas sensor system according to an embodiment of the present invention.

Referring to FIG. 1, the multi-channel resistance-based gas sensor system of the present embodiment may include a multi-channel array 100, a first pre-processing unit 110, a second pre-processing unit 120, a control unit 130, an ADC block 140, or the like.

The multi-channel array 100 may include a heater resistance channel CH1 connected to a temperature sensor (not shown), and a plurality of gas sensor channels (CH2 to CH8) respectively connected to a plurality of resistive type gas sensors (not shown). The above gas sensors may be coated with different reactants that exhibit different reactions depending on gases (e.g., CO gas, $O_2$ gas, and the like).

The first pre-processing unit 110 is configured to select one of a current mode, a resistance mode, and an external resistance mode, analyze a sensing value obtained from the heater resistance channel CH1, and output a first voltage value corresponding to the analysis result to the ADC block 140.

To this end, the first pre-processing unit 110 may include a first mode unit 111, a second mode unit 112, a third mode unit 113 and a first current source determination unit 114. The first mode unit 111 has a current digital-to-analog converter (DAC) 1111 and a first switch 1113 that connects a heater resistance channel line and the current DAC 1111. The second mode unit 112 has a resistance DAC 1121 and a second switch 1123 that connects the heater resistance channel line and the resistance DAC 1121. The third mode unit 113 has an external resistance 1131 connected to the heater resistance channel line. Here, the external resistance 1131 may be configured to be detachably inserted.

The current mode is selected (executed) when the first switch 1113 is switched on and the second switch 1123 is switched off. The resistance mode is selected (executed) when the first switch 1113 is switched off and the second switch 1123 is switched on. The external resistance mode is selected (executed) when both of the first switch 1113 and the second switch 1123 are switched off.

Further, the current mode may be used for analyzing a sensing value smaller than or equal to a preset first resistance value (e.g., resistance value of 1 M ohms or smaller). The external resistance mode may be used for analyzing a sensing value equal to or greater than a preset second resistance value (e.g., resistance value of 10 M ohms or greater). The resistance mode may be used for analyzing a sensing value (e.g., resistance value between 1 M ohm and 10 M ohm) between the preset first resistance value and the preset second resistance value (e.g., resistance value of 10 M ohms or greater). Here, the preset second resistance value is relatively greater than the preset first resistance value.

In other words, in a state of the default setting of the current mode (that is, the first switch 1113 is switched on and the second switch 1123 is switched off), the current mode is maintained when the sensing value (resistance value) of the heater resistance channel CH1 detected by the temperature sensor is 1 M ohm or smaller. The current mode is switched to the resistance mode (that is, the first switch 1113 is switched off and the second switch 1123 is switched on) when the sensing value (resistance value) of the heater resistance channel CH1 is between 1 M ohm and 10 M ohm. The current mode is switched to the external resistance mode (that is, both of the first switch 1113 and the second switch 1123 are switched off) when the sensing value (resistance value) of the heater resistance channel CH1 is 10 M ohm or greater.

The first current source determination unit 114 may be configured to determine a required current source for analyzing the sensing value (sensing value of the CH1 channel) detected by the temperature sensor. When the resistance range of the gas sensor is obtained by using the current DAC in order to determine the required current source, using the general SAR digital logic may cause a sudden high voltage to thereby damage the circuit. Thus, in this embodiment, the circuit is prevented from being damaged by using a separate high voltage protection algorithm.

Figure 2:
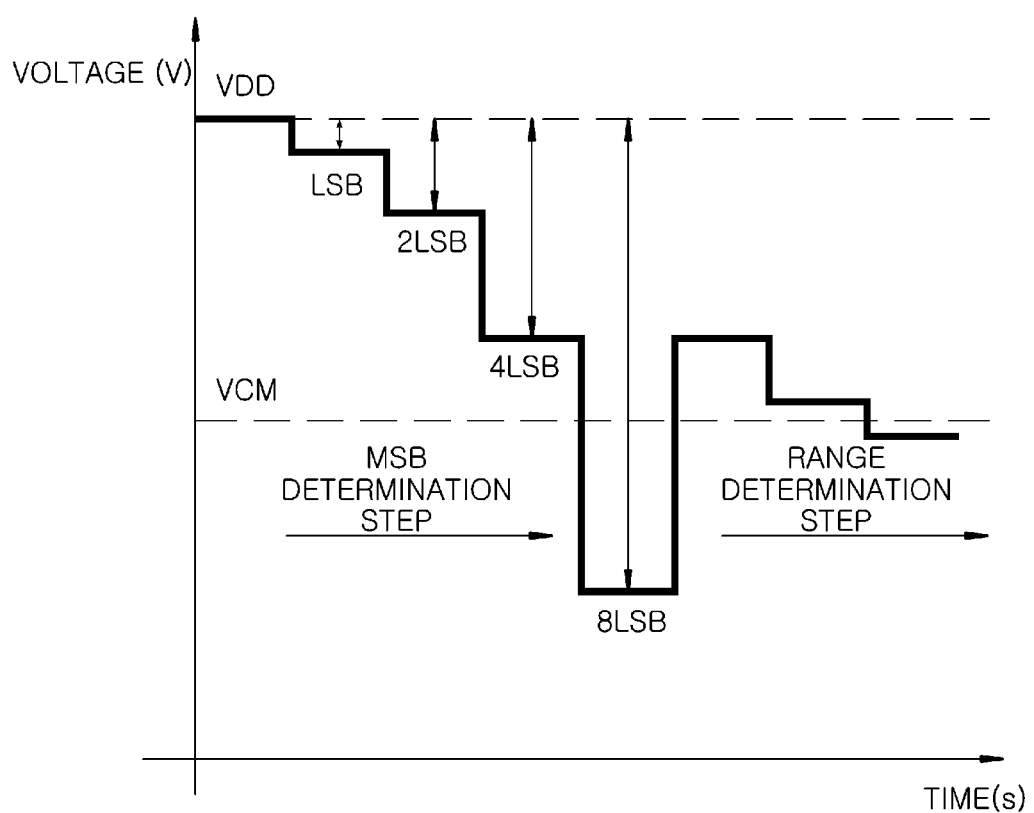
FIG. 2 is a graph for explaining determination of a current value through binary research according to the embodiment of the present invention.

As shown in FIG. 2, for example, the first current source determination unit 114 determines the required current source for analyzing the sensing value (sensing value of the CH1 channel) detected by the temperature sensor while sequentially switching on a plurality of current sources having different current capacities from the least significant bit (LSB) current source having the least current capacity to the next upper significant bit current source.

Referring to FIG. 2, according to the high voltage protection algorithm described above, the current sources sequentially are turned on one by one from the LSB current source, and when the voltage exceeds the VCM (half of the total voltage), the current source at the point beyond the VCM is set to the most significant bit (MSB) current source and the current value is determined through the binary research. In this manner, a high voltage exceeding the maximum voltage is not applied to the circuit when a resistance value within a supportable range is connected to the circuit.

To this end, the first current source determination unit 114 may include a first voltage comparator 1141 configured to compare a first voltage value with a preset reference voltage value and a first SAR digital logic unit 1143 configured to output preset n-bit number of digital data sequentially from the least significant bit to the most significant bit based on whether an output of the first voltage comparator 1141 is high or low.

The output value (OUT<1>) of the first SAR digital logic unit 1143 is transmitted to the control unit 130. The control unit 130 is configured to maintain the current mode (that is, the first switch 1113 is switched on and the second switch 1123 is switched off) when the output value (OUT<1>) is, e.g., 1 M ohm or smaller, switch the current mode to the resistance mode (that is, the first switch 1113 is switched off and the second switch 1123 is switched on) when the output value (OUT<1>) is between, e.g., 1 M ohms and 10 M ohms, and switch the current mode to the external resistance mode (that is, the first and the second switch 1113 and 1123 are switched off) when the output value (OUT<1>) is, e.g., 10 M ohms or greater.

In other words, the control unit 130 may include a microprocessor for performing overall control of a multi-channel resistance-based gas sensor system, or the like such that the first pre-processing unit 110 is controlled by the control unit 130 to execute one of the current mode, the resistance mode, and the external resistance mode based on the output value (OUT<1>) of the first SAR digital logic unit 1143.

Further, the first pre-processing unit 110 may further include an internal temperature sensor 115, a multiplexer 116, or the like. The internal temperature sensor 115 is configured to sense an inner temperature of an apparatus including the gas sensor system or an inner temperature of a space where the gas sensor system is disposed. The multiplexer 116 configured to alternately output the first voltage value and the voltage value corresponding to the sensed inner temperature to the first ADC 142 in the ACD block 140.

The first ADC 142 in the ADC block 140 is configured to convert an analog voltage value of the resistive type heater (or an analog voltage value corresponding to the sensed inner temperature) inputted through the multiplexer 116 to digital data (OUT<3>) and transmit the digital data (OUT<3>) to the control unit 130. The control unit 130 identifies the magnitude of the heater resistance using the digital data (OUT<3>) and accurately controls the amount of heat generation. In other words, since the amount of heat generation is in proportional to the square of the current and the resistance, it is required to accurately define the heater resistance value in order to accurately define the value of the current to be supplied to heat the heater under the control of the control unit.

Next, the second pre-processing unit 120 is configured to select one of the current mode, the resistance mode, and the external resistance mode, analyze a sensing value (sensing value of the resistive type gas sensor) obtained from any one of the gas sensor channels CH2 to CH8, and output a second voltage value corresponding to the analysis result to the ADC block 140.

To this end, the second pre-processing unit 120 may include a first mode unit 122, a second mode unit 123, a third mode unit 124 and a second current source determination unit. The first mode unit 122 has a multiplexer 121, a current DAC 1221 and a first switch 1223 that connects a gas sensor channel line and the current DAC 1221. The second mode unit 123 has a resistance DAC 1231 and a second switch 1233 that connects the gas sensor channel line and the resistance DAC 1231. The third mode unit 124 has an external resistance 1241 connected to the gas sensor channel line. Here, the external resistance 1241 may be configured to be detachably inserted.

The current mode is selected (executed) when the first switch 1223 is switched on and the second switch 1233 is switched off. The resistance mode is selected (executed) when the first switch 1223 is switched off and the second switch 1233 is switched on. The external resistance mode is selected (executed) when both of the first switch 1223 and the second switch 1233 are switched off.

Further, the current mode may be used for analyzing a sensing value smaller than or equal to a preset first resistance value (e.g., resistance value of 1 M ohms or smaller). The resistance mode may be used for analyzing a sensing value (e.g., resistance value between 1 M ohm and 10 M ohm) between the preset first resistance value and a preset second resistance value (e.g., resistance value of 10 M ohms or greater). The external resistance mode may be used for analyzing a sensing value equal to or greater than the preset second resistance value (e.g., resistance value of 10 M ohms or greater). Here, the preset second resistance value is relatively greater than the preset first resistance value.

In other words, in a state of the default setting of the current mode (that is, the first switch 1223 is switched on and the second switch 1233 is switched off), the current mode is maintained when the sensing value (resistance value) of any one of the gas sensor channels CH2 to CH8 detected by the sensor is 1 M ohm or smaller. The current mode is switched to the resistance mode (that is, the first switch 1223 is switched off and the second switch 1233 is switched on) when the sensing value (resistance value) of any one of the gas sensor channels CH2 to CH8 is between 1 M ohm and 10 M ohm. The current mode is switched to the external resistance mode (that is, both of the first switch 1223 and the second switch 1233 are switched off) when the sensing value (resistance value) of any one of the gas sensor channels CH2 to CH8 is 10 M ohm or greater.

The second current source determination unit 125 may be configured to determine a required current source for analyzing the sensing value (sensing value of any one of the channels CH2 to CH8) detected by the gas sensor while sequentially switching on a plurality of current sources having different current capacities from the least significant bit (LSB) current source having the least current capacity to the next upper significant bit current source.

To this end, the second current source determination unit 125 may include a second voltage comparator 1251 configured to compare a second voltage value with a preset reference voltage value and a second SAR digital logic unit 1253 configured to output preset n-bit number of digital data sequentially from the least significant bit to the most significant bit based on whether an output of the second voltage comparator 1251 is high or low.

The output value (OUT<2>) of the second SAR digital logic unit 1253 is transmitted to the control unit 130. The control unit 130 is configured to maintain the current mode (that is, the first switch 1223 is switched on and the second switch 1233 is switched off) when the output value (OUT<2>) is, e.g., 1 M ohm or smaller, switches the current mode to the resistance mode (that is, the first switch 1223 is switched off and the second switch 1233 is switched on) when the output value (OUT<2>) is between, e.g., 1 M ohms and 10 M ohms, and switch the current mode to the external resistance mode (the first switch 1223 and the second switch 1233 are switched off) when the output value (OUT<2>) is, e.g., 10 M ohms or greater.

In other words, the control unit 130 controls the second pre-processing unit 120 to execute one of the current mode, the resistance mode, and the external resistance mode based on the output value (OUT<2>) of the second SAR digital logic unit 1253.

The second ADC 144 in the ADC block 140 is configured to convert the analog voltage value (sensing value of the gas sensor channel) transmitted from the second pre-processing unit 120 to digital data (OUT<4>).

In the embodiment of the present invention, the output value of the first pre-processing unit is defined as the first voltage value, and the output value of the second pre-processing unit is defined as the second voltage value. However, this is merely an example for convenience of description and better understanding, and the present invention is not limited thereto. The second pre-processing unit can be defined as the first pre-processing unit, and the first pre-processing unit can be defined as the second pre-processing unit. The first voltage value can be defined as the second voltage value, and the second voltage value can be defined as the first voltage value. In that case, the terms for the components of the first pre-processing unit and the second pre-processing unit and for the two ADCs in the ADC block may be changed in the same manner.

The above description is merely exemplary description of the technical scope of the present invention, and it will be understood by those skilled in the art that various changes and modifications can be made without departing from original characteristics of the present invention. In other words, the embodiments disclosed in the present invention are intended to explain, not to limit, the technical scope of the present invention, and the technical scope of the present invention is not limited by the embodiments.

Therefore, the protection scope of the present invention should be interpreted based on the following claims and it should be appreciated that all technical scopes included within a range equivalent thereto are included in the protection scope of the present invention.

What is claimed is:

1. A multi-channel resistance-based gas sensor system comprising:
   a multi-channel array including a plurality of gas sensor channels respectively connected to a plurality of resistive type gas sensors;
   a first pre-processing unit configured to select one of a current mode, a resistance mode, and an external resistance mode, analyze, based on the selected mode, a sensing value obtained from any one of the gas sensor channels among multiple sensing values detected by the resistive type gas sensors, and output a first voltage value corresponding to the analysis result;
   a first analog-to-digital converter (ADC) configured to convert the first voltage value to digital data; and
   a control unit configured to control the first pre-processing unit to execute one of the current mode, the resistance mode, and the external resistance mode,
   wherein the current mode is used for analyzing, among the multiple sensing values, a sensing value that is smaller than or equal to a preset first resistance value,
   the external resistance mode is used for analyzing, among the multiple sensing values, a sensing value that is greater than or equal to a preset second resistance value that is greater than the preset first resistance value, and
   the resistance mode is used for analyzing, among the multiple sensing values, a sensing value that is greater than the preset first resistance value and smaller than the preset second resistance value, wherein the first pre-processing unit includes:
a first mode unit having a current digital-to-analog converter (DAC) and a first switch that connects a channel line for the gas sensors and the current DAC;
a second mode unit having a resistance DAC and a second switch that connects the channel line for the gas sensors and the resistance DAC; and
a third mode unit having an external resistance connected to the channel line for the gas sensors.

2. The multi-channel resistance-based gas sensor system of claim 1, wherein the first mode unit selects the current mode when the first switch is switched on and the second switch is switched off.

3. The multi-channel resistance-based gas sensor system of claim 1, wherein the second mode unit selects the resistance mode when the first switch is switched off and the second switch is switched on.

4. The multi-channel resistance-based gas sensor system of claim 1, wherein the third mode unit selects the external resistance mode when both of the first switch and the second switch are switched off.

5. The multi-channel resistance-based gas sensor system of claim 1, wherein the first pre-processing unit further includes:
a first current source determination unit configured to determine a current source required for analyzing each of the sensing values detected by the resistive type gas sensors while sequentially switching on a plurality of current sources having different current capacities from the least significant bit current source (LSB current source) having the least current capacity to the next upper significant bit current source.

6. The multi-channel resistance-based gas sensor system of claim 5, wherein the first current source determination unit includes:
a first voltage comparator configured to compare the first voltage value with a preset reference voltage value; and
a first SAR digital logic unit configured to output preset n-bit number of digital data sequentially from the least significant bit to the most significant bit based on whether an output of the first voltage comparator is high or low.

7. The multi-channel resistance-based gas sensor system of claim 1, wherein the multi-channel array further includes:
at least one heater resistance channel connected to a temperature sensor,
the multi-channel resistance-based gas sensor system further comprising:
a second pre-processing unit configured to select one of the current mode, the resistance mode, and the external resistance mode, analyze a sensing value obtained from the heater resistance channel based on the selected mode, and output a second voltage value corresponding to the analysis result; and
a second analog-to-digital converter (ADC) configured to convert the second voltage value to digital data.

8. The multi-channel resistance-based gas sensor system of claim 7, wherein the second pre-processing unit includes:
a first mode unit having a current digital-to-analog converter (DAC) and a first switch that connects a channel line for heater resistance and the current DAC;
a second mode unit having a resistance DAC and a second switch that connects the channel line for the heater resistance and the resistance DAC; and
a third mode unit having an external resistance connected to the channel line for the heater resistance.

9. The multi-channel resistance-based gas sensor system of claim 8, wherein the first mode unit selects the current mode when the first switch switched is on and the second switch is switched off.

10. The multi-channel resistance-based gas sensor system of claim 8, wherein the second mode unit selects the resistance mode when the first switch is switched off and the second switch is switched on.

11. The multi-channel resistance-based gas sensor system of claim 8, wherein the third mode unit selects the external resistance mode when both of the first switch and the second switch are switched off.

12. The multi-channel resistance-based gas sensor system of claim 8, wherein the second pre-processing unit further includes:
a second current source determination unit configured to determine a current source required for analyzing the sensing value detected by the temperature sensor while sequentially switching on a plurality of current sources having different current capacities from the least significant bit current source (LSB current source) having the least current capacity to the next upper significant bit current source.

13. The multi-channel resistance-based gas sensor system of claim 12, wherein the second current source determination unit includes:
a second voltage comparator configured to compare the second voltage value with a preset reference voltage value; and
a second SAR digital logic unit configured to output preset n-bit number of digital data sequentially from the least significant bit to the most significant bit based on whether an output of the second voltage comparator is high or low.

* * * * *